(12) United States Patent
Ranganathan

(10) Patent No.: US 8,481,025 B2
(45) Date of Patent: *Jul. 9, 2013

(54) COMPOSITION FOR MAINTAINING HEALTHY KIDNEY FUNCTION

(75) Inventor: Natarajan Ranganathan, Broomall, PA (US)

(73) Assignee: Kibow Biotech, Inc., Newtown Square, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/602,386

(22) Filed: Sep. 4, 2012

(65) Prior Publication Data

US 2012/0328573 A1    Dec. 27, 2012

Related U.S. Application Data

(63) Continuation of application No. 12/407,201, filed on Mar. 19, 2009, now Pat. No. 8,257,693, which is a continuation of application No. 10/936,262, filed on Sep. 8, 2004, now abandoned, which is a continuation-in-part of application No. PCT/US02/07554, filed on Mar. 13, 2002.

(51) Int. Cl.
*C12N 1/20* (2006.01)

(52) U.S. Cl.
USPC .............. 424/93.3; 424/93.45; 424/93.44; 424/93.4; 424/738; 435/252.4; 435/252.9; 435/253.4

(58) Field of Classification Search
None
See application file for complete search history.

(56) References Cited

U.S. PATENT DOCUMENTS

| | | | |
|---|---|---|---|
| 4,022,883 A | 5/1977 | Setala | |
| 4,218,541 A | 8/1980 | Ackerman | |
| 4,970,153 A | 11/1990 | Kobashi et al. | |
| 5,116,737 A | 5/1992 | McCoy | |
| 5,258,181 A | 11/1993 | Cregier et al. | |
| 5,716,615 A | 2/1998 | Vesely et al. | |
| 5,952,021 A * | 9/1999 | Santus | 426/34 |
| 6,306,442 B1 * | 10/2001 | Sunvold et al. | 424/725 |
| 7,998,470 B2 * | 8/2011 | Ranganathan | 424/93.1 |
| 8,257,693 B2 * | 9/2012 | Ranganathan | 424/93.3 |

FOREIGN PATENT DOCUMENTS

| | | |
|---|---|---|
| WO | WO 99/49877 | 10/1999 |
| WO | WO 00/74689 A1 | 6/2000 |
| WO | WO 00/71138 A2 | 11/2000 |
| WO | WO 00/71139 A2 | 11/2000 |
| WO | WO 00/72855 * | 12/2000 |
| WO | WO 00/74712 | 12/2000 |

OTHER PUBLICATIONS

Gibson et al., "Dietary Modulation of the Human Colonic Microbiota:Introducing the Concept of Prebiotics", J. Nutr. 1995 125:1401-1412.

* cited by examiner

*Primary Examiner* — Susan Hoffman
(74) *Attorney, Agent, or Firm* — Licata & Tyrell P.C.

(57) ABSTRACT

The present invention provides a composition comprising prebiotic and probiotic components and is used to reduce elevated levels of nitrogenous waste products and to promote a healthy bowel microenvironment.

5 Claims, 1 Drawing Sheet

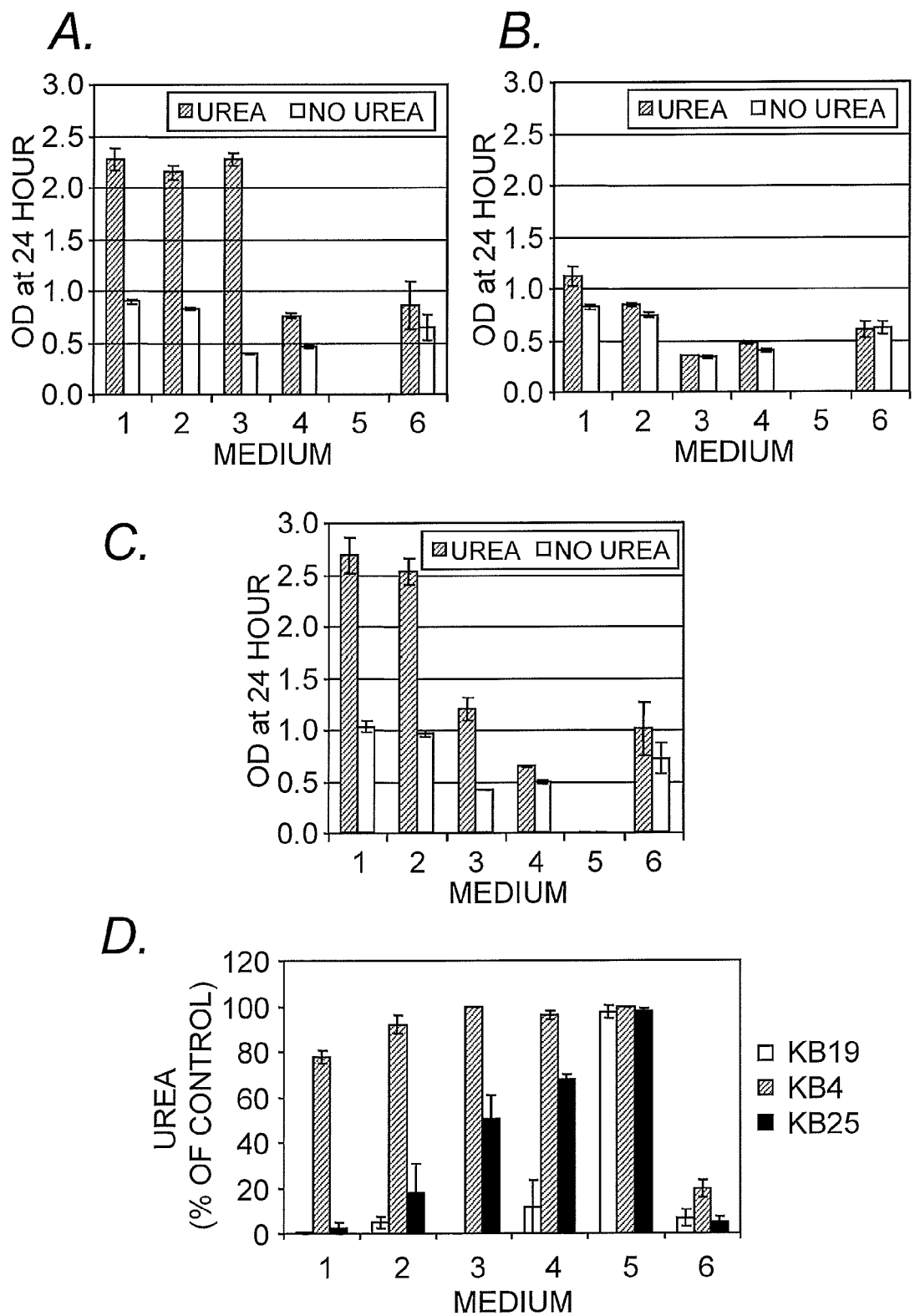

COMPOSITION FOR MAINTAINING HEALTHY KIDNEY FUNCTION

This application is a continuation of Ser. No. 12/407,201 filed Mar. 19, 2009, now U.S. Pat. No. 8,257,693, which is a continuation of U.S. Ser. No. 10/936,262 filed Sep. 8, 2004, now abandoned, which is a continuation-in-part of U.S. Serial No. PCT/US2002/007554 filed Mar. 13, 2002.

FIELD OF THE INVENTION

The present invention relates to compositions and methods which reduce the concentration of nitrogenous wastes. The compositions may be in the form of a food product, dietary supplement, medical food or drug.

BACKGROUND OF THE INVENTION

One of the main functions of the normal, healthy kidney, besides its regulatory, endocrine, and metabolic functions, is the disposal of waste products. Any impairment of excretory function can lead to the accumulation of a variety of nitrogenous waste products including, urea, creatinine and uric acid. High concentrations of waste products in the blood stream can exacerbate renal failure and promote kidney stones. Moreover, nitrogenous solutes in the circulating blood promote osmotic diffusion into the lumen because of the concentration gradient across the intestinal wall. This diffusion mechanism led to the concept of oral sorbents to augment gut-based clearance of nitrogenous waste products. Sorbents or microbes have demonstrated their ability to remove various compounds and nitrogenous wastes within the large bowel.

Urea-specific sorbents such as synthetic polymers and modified polysaccharides have been evaluated for the removal of urea and other nitrogenous wastes via the gut. Other sorbents such as oxidized starch, activated charcoal, and carob flour have also been investigated for the in vivo elimination of uremic toxins with some success. Prakash & Chang ((1996) *Nature Medicine* 2:883-88) demonstrated that microencapsulated, genetically-engineered *E. coli* DH5 are effective in removing urea and ammonia in an in vitro system. The same researchers obtained similar results in oral administration of *E. coli* DH5 cells in a uremic rat animal model. Bliss et al. ((1996) *Am. J. Clin. Nutr.* 63:392-398) have demonstrated that supplemental gum arabic fiber increases fecal nitrogen excretion and lowers urea nitrogen concentration in chronic renal failure patients consuming a low protein diet. Reinhart et al. ((1998) *Rec. Adv. In Canine and Feline Nutr. Iams Nutrition Symposium Proceedings*. Vol. II:395-404) found that canine renal patients fed a diet containing a fermentable fiber blend improved clinical end-stage renal disease status, suggesting that specific nutritional alteration allows repartitioning of nitrogen excretion away from the kidney and into the feces by colonic fermentation or additional bacterial growth.

Prebiotic components are food ingredients that enhance the actions of probiotic components in the digestive tract. In this synergistic or synbiotic relationship a probiotic component, such as *Bifidobacteria*, metabolizes undigested carbohydrates, such as dietary fibers, oligosaccharides, etc., to produce short-chain fatty acids such as acetate, propionate and butyrate. These short-chain fatty acids may promote intestinal cell growth, enhance water and mineral absorption, and prevent yeast, mold, and pathogenic bacterial growth. In addition, probiotic components may antagonize pathogens directly through production of antimicrobial and antibacterial compounds such as cytokines and butyric acid (De Vuyst and Vandamme. Antimicrobial potential of lactic acid bacteria. In: De Vuyst L, Vandamme E L, eds. Bacteriocins of lactic acid bacteria. Glasgow, United Kingdom: Blackie Academic and Professional; 1994:91-142; Dodd and Gasson. Bacteriocins of lactic acid bacteria. In: Gasson M J, de Vos W M, eds. Genetics and biotechnology of lactic acid bacteria. Glasgow, United Kingdom: Blackie Academic and Professional; 1994: 211-51; Kailasapathy and Chin (2000) *Immunol. Cell. Biol.* 78(1):80-8), reduce gut pH by stimulating the lactic acid-producing microflora (Langhendries et al. (1995) *J. Pediatr. Gastroenterol. Nutr.* 21:177-81), compete for binding and receptor sites that pathogens occupy (Kailasapathy and Chin (2000) *Immunol. Cell. Biol.* 78(1):80-8; Fujiwara et al., (1997) *Appl. Environ. Microbiol.* 63:506-12), improve immune function and stimulate immunomodulatory cells (Isolauri et al. (1991) *Pediatrics* 88:90-97; Isolauri et al. (1995) *Vaccine* 13:310-312; Rolfe (2000) *J. Nufr.* 130(2S): 396S-402S), compete with pathogens for available nutrients and other growth factors (Rolfe (2000) *J. Nufr.* 130(2S):396S-402S), or produce lactase which aids in lactose digestion.

U.S. Pat. No. 4,022,883 discloses a method for alleviating uremic symptoms in persons suffering from renal failure comprising administering orally thereto an effective dosage of a cell mass of a non-pathogenic soil bacteria selected from the group consisting of an urea degrading bacterium, a creatine degrading bacterium, a creatinine degrading bacterium and an uric acid degrading bacterium wherein the urea degrading bacterium is a species of *Serratia*; the creatinine degrading bacterium is a non-fluorescent *Pseudomonas, Rhizobium, Agrobacterium, Corynebacterium ureafaciens, Arthrobacter ureafaciens, E. coli,* or *Pseudomonas aeruginosa*; and a uric acid degrading bacterium is *Bacillus subtilis,* a non-fluorescent *Pseudomonas, Bacillus fastidosus, Micrococcus dentrificans, Mycobacterium phlei, Aerobacter aerogenes.*

U.S. Pat. No. 4,218,541 teaches a method for converting urea to innocuous products. The method involves obtaining a culture of at least one microorganism selected from the group of *Enterobacter agglomerans,* Group D *Streptococcus, Bacilli,* and *Pseudomonad* or mixtures of said microorganisms and adding the culture to a composition containing urea.

U.S. Pat. No. 4,970,153 discloses a method of producing urease and more particularly a method of producing acid urease by the cultivation of *Lactobacillus fermentum* TK 1214. This patent further teaches the use of such acid urease or the decomposition of urea contained in fermentation food products.

U.S. Pat. No. 5,116,737 teaches a method for growing acid-producing bacterial cultures, such as diary cultures, wherein the culture is selected to contain a urease-producing strain of bacteria and the medium used for the culturing contains added urea. Urease-producing strains of *Streptococcus thermophilus* and *Bifidobacterium* are also disclosed.

U.S. Pat. No. 5,716,615 discloses a pharmaceutical composition containing several different bacteria including *Streptococcus thermophilus, Lactobacilli* and *Bifidobacteria* wherein the bacteria are present in the composition at a total concentration of $1 \times 10^{11}$ to $1 \times 10^{13}$ per gram. An excipient consisting of maltodextrin, microcrystalline cellulose, maize starch, levulose, lactose or dextrose is further taught. Methods of using the pharmaceutical composition are also disclosed which include treatment of a gastrointestinal disorder and hypercholesteremia or modulating a host's immune response.

The present invention combines the beneficial effects of prebiotic and probiotic components into a synbiotic product that effectively reduces nitrogenous wastes.

SUMMARY OF THE INVENTION

An object of the present invention is to provide a composition comprising prebiotic and probiotic components. This composition can be added to a food product, dietary supplement, medical food or pharmaceutical product which, upon ingestion, will promote a healthy intestinal microenvironment and assist in the elimination of nitrogenous waste products that can build up in concentration in the circulating blood. Increased concentrations of the wastes are known to exert a negative impact on an individual's physiology and contribute to a decreased sense of well-being and general malaise. Methods for reducing nitrogenous waste products using these products are also provided.

BRIEF DESCRIPTION OF THE DRAWINGS

FIG. 1 shows the effects of nutrient composition and availability on growth and urea hydrolysis by KB19, KB4, and KB25. Panel A, B, and C depict the growth of KB19, KB4, and KB25, respectively, in various combinations of nitrogen and carbon sources in the presence and absence of urea. Panel D depicts the rate of hydrolysis of urea in 24 hours by KB19, KB4 and KB25 grown in various combinations of nitrogen and carbon sources. Medium 1 was supplemented with peptone and 1% sucrose. Medium 2 was supplemented with peptone, ammonium sulfate, and 1% sucrose. Medium 3 was supplemented with ammonium sulfate and 1% sucrose. Medium 4 was supplemented with peptone and 0.1% sucrose. Medium 5 was supplemented with peptone and a polysaccharide. Medium 6 was supplemented with peptone, polysaccharide and 0.1% sucrose.

DETAILED DESCRIPTION OF PREFERRED EMBODIMENTS

Nitrogenous waste products accumulating in the blood stream have detrimental affects on health. Removal of nitrogenous wastes by diverting them into the colon is a viable approach to decrease the negative impact that waste product accumulation has on an individual's physiology. The present invention combines the properties of probiotic and prebiotic components into a synbiotic product to effectively reduce the blood concentration of nitrogenous waste products and has the added beneficial effect of promoting the growth of desirable intestinal microflora.

A probiotic component of the present invention refers to a mono or mixed culture of live or freeze-dried microorganisms which, when applied to man or animal, beneficially affects the host by improving the properties of the indigenous microflora, such as *bifidobacterium* organisms that metabolize undigested carbohydrates and are beneficial to an individual. Probiotic components of the present invention are selected for their ability to exert a beneficial effect on the host, survive transit through the intestinal tract, to adhere to intestinal epithelial cell lining, to produce of anti-microbial substances towards pathogens and/or to stabilize the intestinal microflora. Furthermore, a probiotic component should have a good shelf-life. Synbiotic products of the present invention generally contain a large number of viable cells at the time of consumption, and are non-pathogenic and nontoxic. Examples of probiotic components include, but are not limited to, *Bifidobacterium* spp. (e.g., *bifidum, longum, infantis*), *Lactobacillus* spp. (e.g., *bulgaricus, acidophilus, lactis, helveticus, casei, plantarum, reuteri, delbrueckii, chamnosus, johnsonii, paracasei*), *Streptococcus* spp. (e.g., *thermophilus, diacetilactis, cremoris, durans, faecalis*), *Saccharomyces* spp. (e.g., *pombe, boulardii*), *Leuconostoc* spp. (e.g., *citrovorum, dextranicum*) and *Bacillus* sp. (e.g., *pasteurii*). In one embodiment, the probiotic component is composed of at least one, at least two, or at least three microorganisms from the genera *Bifidobacterium, Lactobacillus, Streptococcus, Saccharomyces, Leuconostoc* and *Bacillus*. In another embodiment, the probiotic component is composed of at least one microorganism from the genera *Bifidobacterium, Streptococcus* or *Lactobacillus*. In a further embodiment, the probiotic component is composed of at least two microorganisms from the genera *Bifidobacterium, Streptococcus* or *Lactobacillus*. In a particular embodiment, the probiotic component is composed of *Bifidobacterium longum, Streptococcus thermophilus* and *Lactobacillus acidophilus*.

Microorganisms also useful in the invention are those that have the ability, either through natural selection or by genetic manipulation, to catabolize various nitrogenous compounds (e.g., urea, creatinine, uric acid and ammonia) by expressing or overexpressing one or more cognate catabolic enzymes. Exemplary microorganisms are those having an elevated level of urease or creatininase secretion.

A microorganism exhibiting elevated levels of catabolic enzyme secretion can be selected or trained by exposing a selected microorganism on increasing amounts of the metabolite of interest (e.g., urea, creatinine, uric acid and ammonia). For example, it has been found that a standard strain of *Streptococcus thermophilus* can be trained to express elevated levels of urease by sequential passage of the strain on increasing amounts of urea, e.g., a single colony growing on 0.5% urea is selected and applied to medium containing 1.0% urea, a single colony growing on 1.0% urea is selected and applied to medium containing 2.0% urea, etc. Using such a method, a *S. thermophilus* strain having the ability to grow on 5% urea was isolated. This strain proliferated in artificial intestinal fluid (AIF, US Pharmacopeia) in the pH range of 5.5 to 7.5, characteristic of the colon environment; used urea as a sole nitrogen source; and catabolized urea in the presence of other nitrogen sources. It was found that urea hydrolysis was growth- and pH-dependent and that urea concentrations could be reduced by this strain from 300 mg/dL to 20 mg/dL within 24 hours at pH 6.3 when inoculated in AIF at an initial density of $10^9$ cfu/mL. Moreover, this strain survived 3 hours in acidic pH 3.0 with only a one-log loss in cfu and was able to pass through bile. In addition, this strain did not appear to exhibit any resistance to eight commonly used antibiotics. Therefore, these data indicate that a specifically selected or trained bacterial isolate can be used as a urea-targeted component in a synbiotic product of the present invention.

Elevated levels of secretion can also be obtained by overexpressing the gene of interest (e.g., via multiple copies or a promoter driving high levels of expression) in a prokaryotic microorganism of interest such as *Bifidobacterium, Lactobacillus, Streptococcus, Leuconostoc* or *Bacillus*, or a eukaryotic microorganism such as *Saccharomyces*. The gene of interest can be under the regulatory control of an inducible or constitutive promoter. Promoters for use in recombinant prokaryotic expression vectors are well-established in the art and can include the beta-lactamase (penicillinase) and lactose promoter systems (Chang et al. (1978) *Nature* 275:615; Goeddel et al. (1979), *Nature* 281:544), a tryptophan (trp) promoter system (Goeddel et al. (1980) *Nucleic Acids Res.* 8:4057; EPO App. Publ. No. 36,776) and the tac promoter (De Boer et al. (1983) *Proc. Natl. Acad. Sci. USA* 80:21). While these are commonly used promoters which are commercially available, one of skill in the art can appreciate that any other suitable microbial promoter can be used as well. Nucleic acid sequences encoding suitable prokaryotic promoters have been published thereby enabling one of skill in the art to readily isolate these promoters (e.g., by standard cloning or PCR methodologies) for cloning into plasmid or viral vectors (Siebenlist et al. (1980) Cell 20:269). The promoter and Shine-Dalgarno sequence (for prokaryotic host expression) are operably-linked to the DNA encoding the gene of interest, i.e., they are positioned so as to promote transcription of the messenger RNA from the DNA, and subsequently introduced into a suitable host cell.

Eukaryotic microbes such as yeast cultures can also be transformed with suitable protein-encoding vectors. See e.g., U.S. Pat. No. 4,745,057. *Saccharomyces cerevisiae* is the most commonly used among lower eukaryotic host microorganisms, although a number of other strains are commonly available. Yeast vectors can contain an origin of replication from the 2 micron yeast plasmid or an autonomously replicating sequence (ARS), a promoter, DNA encoding the desired protein, sequences for polyadenylation and transcription termination, and a gene encoding for a selectable marker. An exemplary plasmid is YRp7, (Stinchcomb et al. (1979) *Nature* 282:39; Kingsman et al. (1979) *Gene* 7:141; Tschemper et al. (1980) *Gene* 10:157). This plasmid contains the trp1 gene, which provides a selection marker for a mutant strain of yeast lacking the ability to grow in tryptophan, for example ATCC No. 44076 or PEP4-1 (Jones (1977) *Genetics* 85:12). The presence of the trp1 lesion in the yeast host cell genome then provides an effective environment for detecting transformation by growth in the absence of tryptophan.

Suitable promoting sequences in yeast vectors include the promoters for metallothionein, 3-phospho-glycerate kinase (Hitzeman et al. (1980) *J. Biol. Chem.* 255:2073) or other glycolytic enzymes (Hess et al. (1968) *J. Adv. Enzyme Reg.* 7:149; Holland et al. (1978) *Biochemistry* 17:4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are commercially available and further described in Hitzeman et al., EP 73,657.

As will be understood by those of skill in the art, expression vectors containing polynucleotides which encode a degradative enzyme of interest, e.g., a urease or creatininase, can be designed to contain signal sequences which direct secretion of enzyme of interest through a prokaryotic or eukaryotic cell membrane. Such signal sequences are well-established in the art and can be taken from other enzymes/proteins known to be secreted into the extracellular environment.

Transforming the microorganisms as defined herein, describes a process by which exogenous DNA is introduced into and changes a recipient cell. It can occur under natural or artificial conditions using various methods well-known in the art. Transformation can rely on any known method for the insertion of foreign nucleic acid sequences into a prokaryotic or eukaryotic host cell. The method is selected based on the type of host cell being transformed and can include, but is not limited to, viral infection, electroporation, heat shock, lipofection, and particle bombardment. Such "transformed" cells include stably-transformed cells in which the inserted DNA is capable of replication either as an autonomously replicating plasmid or as part of the host chromosome. This also includes cells which transiently express the inserted DNA or RNA for limited periods of time.

As will be appreciated by the skill artisan, a microorganism can also be exposed to a mutagen to cause changes in the genetic structure of the organism so that it expresses elevated levels of a catabolic enzyme of interest.

Transformed or mutagenized strains are subsequently selected for the ability to grow in the presence of the metabolite which is degraded by the catabolic enzyme of interest. By way of example, a strain transformed with nucleic acid sequences encoding a urease is selected for high levels of urease secretion by growing said strain on high levels of urea. Levels of urease secretion can also be detected using standard enzymatic assays. As disclosed herein, the strain can be sequentially subcultured on increasing levels of urea to further enhance urease secretion. One embodiment of the present invention provides a urease-secreting strain of *Bacillus pasteurii, Streptococcus thermophilus* or *Saccharomyces pombe*. In another embodiment, a urease-secreting strain is at least one of the microorganisms of a probiotic component composed of at least two or at least three microorganisms. In a further embodiment, a urease-secreting strain is at least two of the microorganisms of a probiotic component composed of at least three microorganisms.

The probiotics according to the invention can be obtained by fermentation and can be stored after fermentation and before addition to the synbiotic composition of the present invention for a time and at a temperature that prevents substantial loss of probiotic cfu. For example, the probiotic component can be fermented until a final concentration of $10^6$ to $5 \times 10^{10}$, or $10^7$ to $10^{10}$, or $10^8$ to $10^9$ cfu per mL of fermented medium is achieved.

When the probiotic component is a mono culture, said mono culture is 100% of the probiotic component. When the probiotic component is composed of at least two microorganisms, each microorganism can be 10, 15, 20, 30, 40, 50, 60, 70, 80, or 90% of the probiotic component, wherein the total of all microorganisms is 100%. An exemplary probiotic component is composed of about 10-15% *L. acidophilus*, about 10-15% *B. longum* and about 70-80% *S. thermophilus* (e.g., a ratio of approximately 1:1:8, respectively).

As used herein, the probiotic component or urease-secreting microorganism is one component or additive to a food product or to an enterically coated tablet, capsule, powder, soft gel, gelcap, or liquid. Accordingly, the probiotic component or urease-secreting microorganism is included at a concentration of $10^8$ cfu/mL, $10^9$ cfu/mL, $10^{10}$ cfu/mL, $10^{11}$ cfu/mL, or $10^{12}$ cfu/mL when added as a liquid or $10^8$ cfu/g, $10^9$ cfu/g, $10^{10}$ cfu/g, $10^{11}$ cfu/g, or $10^{12}$ cfu/g when added as a freeze-dried powder. In one embodiment, the probiotic component is about 20% to about 70% of the total synbiotic product weight, In particular embodiments, the probiotic component is about 50% of the total synbiotic product weight.

A prebiotic component of the present invention refers to a non-digestive food that beneficially affects the host by selectively stimulating the growth and/or activity of one or more non-pathogenic bacteria in the colon. Prebiotic components of the present invention are considered to have anti-carcinogenic, anti-microbial, hypolipidemic and glucose modulatory activities. They can also improve mineral absorption and balance. Furthermore, bacteria belonging to the *Bifidobacterium* and *Lactobacillus* families are stimulated by the presence of the prebiotic component and proliferate. Pharmacokinetically, the prebiotic components reach the colon largely intact. An exemplary prebiotic component includes, but is not limited to, an oligosaccharide such as fructo-oligosaccharide or inulin, isomaltose oligosaccharide, trans-galacto-oligosaccharide, xylo-oligosaccharide, or soy-oligosaccharide; a pyrodextrin such as arabinogalactan, lactilol, lactosucrose, or lactulose; or a fiber source such as oat gum, pea fiber, apple fiber, pectin, guar gum, psyllium husks, glucomannan or guar gum hydrolysate (BeneFiber, Novartis Pharmaceuticals). In one embodiment, the prebiotic component is composed of at least one, at least two, or at least three non-digestive foods (e.g., oligosaccharides, pyrodextrins or a fiber source). In another embodiment, an oligosaccharide is at least one of the non-digestive foods of a prebiotic component composed of at least two or at least three non-digestive foods. In yet another embodiment, a fiber source is at least one of the non-digestive foods of a prebiotic component composed of at least two or at least three non-digestive foods. In a further embodiment, a fiber source is at least two of the non-digestive foods of a prebiotic component composed of at least three non-digestive foods. In a still further embodiment, the prebiotic component is composed of at least one of the following non-digestive foods of lactulose, psyllium husks and guar gum hydrolysate. In particular embodiments, the prebiotic component is composed of lactulose, psyllium husks and guar gum hydrolysate.

When the prebiotic component is a single non-digestive food, said non-digestive food is 100% of the prebiotic component. When the prebiotic component is composed of two or more non-digestive foods, each non-digestive food can be 5, 10, 15, 20, 30, 40, 50, 60, 70, 80, or 90% of the prebiotic component, wherein the non-digestive food total is 100%. An exemplary prebiotic component is composed of about 5-30% by weight of lactulose, 5-30% by weight of psyllium husks, and 5-30% by weight of guar gum hydrolysate.

The amount of prebiotic component added to the probiotic component is 100 milligrams per serving, 500 milligrams per serving, 1 gram per serving, 5 grams per serving or 10 grams per serving. In one embodiment, the prebiotic component is not less than 100 milligrams and not more than 10 grams per serving. In one embodiment, the prebiotic component is about 20% to about 70% of the total synbiotic product weight, In particular embodiments, the prebiotic component is about 50% of the total synbiotic product weight. When the synbiotic product further includes addition additives, the percent of the prebiotic and/or probiotic component can be decreased to accommodate the additional additive. In particular embodiments, the percent of the prebiotic component is decreased to accommodate the additional additive.

A synbiotic product combining the beneficial properties of probiotic and prebiotic components can include a food product, dietary supplement, comestible medical food or pharmaceutical product. In the context of the present invention, "synbiotic" refers to a mixture of at least one probiotic and at least one prebiotic components to promote health enhancing effects (Gibson and Roberfroid (1995) *J. Nutr.* 125:1401-1412). The ingestion of said synbiotic product reduces the blood concentration of nitrogenous waste products that accumulate in the circulating blood stream. These waste products of the present invention can be of an endogenous origin such as normal or abnormal metabolic routes or bacterial putrefaction. Furthermore, the waste products can be of an exogenous origin as in dietary intake of proteins and amino acids. Furthermore, repeated ingestion of the synbiotic product will have a highly beneficial effect upon the intestinal microflora by localization and colonization in the large intestine of microbes known to promote a healthy intestinal microenvironment.

As indicated herein, a synbiotic product of the present invention can take the form of a food product including, but is not limited to, a health bar, health drink, yogurt, dahi, or sachet or an enterically coated tablet, capsule, powder, soft gel, gelcap, or liquid. In addition to containing at least one, at least two or at least three prebiotic and probiotic components, the symbiotic product of the present invention can further containing various fillers or additives.

Optional additives of the present composition include, without limitation, pharmaceutical excipients such as magnesium stearate, talc, starch, sugars, fats, antioxidants, amino acids, proteins, nucleic acids, electrolytes, vitamins, derivatives thereof or combinations thereof. In one embodiment, an additive of the synbiotic product is carob flour, for example, locust bean gum. In another embodiment, an additive is a mushroom extract from *Agaricus bisporus*. In particular embodiments, a gel cap contains fillers such as magnesium stearate, talc and starch.

Further, to increase the palatability of a food product containing a prebiotic and probiotic, it may be desirable to add flavors, sweetening agents, binders or bulking agents.

Flavors which can optionally be added to the present compositions are those well-known in the pharmaceutical art. Examples include, but are not limited to, synthetic flavor oils, and/or oils from plants leaves, flowers, fruits and so forth, and combinations thereof are useful. Examples of flavor oils include, but are not limited to, spearmint oil, peppermint oil, cinnamon oil, and oil of wintergreen (methylsalicylate). Also useful are artificial, natural or synthetic fruit flavors such as citrus oils including lemon, orange, grape, lime, and grapefruit, and fruit essences including apple, strawberry, cherry, pineapple and so forth.

Sweetening agents can be selected from a wide range of materials such as water-soluble sweetening agents, water-soluble artificial sweeteners, and dipeptide-based sweeteners, including salts thereof and mixtures thereof, without limitation.

Binders can be selected from a wide range of materials such as hydroxypropylmethylcellulose, ethylcellulose, or other suitable cellulose derivatives, povidone, acrylic and methacrylic acid co-polymers, pharmaceutical glaze, gums (e.g., gum tragacanth), milk derivatives (e.g., whey), starches (e.g., corn starch) or gelatin, and derivatives, as well as other conventional binders well-known to persons skilled in the art. Examples of bulking substances include, but are not limited to, sugar, lactose, gelatin, starch, and silicon dioxide.

When the above-mentioned additives are included in the synbiotic product of the present invention, they are generally less than 15% of the total synbiotic product weight. In particular embodiments, they are less than 5 to 10% of the total synbiotic product weight.

To facilitate targeting of the synbiotic product of the present invention to the gastrointestinal tract, there a number of controlled release formulations that are developed preferably for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems can be found in Yie W. Chien, Novel Drug Delivery Systems, 1992 (Marcel Dekker, Inc.).

For example, enteric coatings are applied to tablets to prevent the release of drugs in the stomach either to reduce the risk of unpleasant side effects or to maintain the stability of the drug which might otherwise be subject to degradation of expose to the gastric environment. Most polymers that are used for this purpose are polyacids that function by virtue or the fact that their solubility in aqueous medium is pH-dependent, and they require conditions with a pH higher than normally encountered in the stomach. One desirable type of oral controlled release structure is enteric coating of a solid or liquid dosage form. Enteric coatings promote the compounds remaining physically incorporated in the dosage form for a specified period when exposed to gastric juice. Yet the enteric coatings are designed to disintegrate in intestinal fluid for ready absorption. Delay of absorption is dependent on the rate of transfer through the gastrointestinal tract, and so the rate of gastric emptying is an important factor. Some investigators have reported that a multiple-unit type dosage form, such as granules, may be superior to a single-unit type.

Typical enteric coating agents include, but are not limited to, hydroxypropylmethylcellulose phthalate, methacrylic acid-methacrylic acid ester copolymer, polyvinyl acetate-phthalate and cellulose acetate phthalate (Hasegawa, (1985) *Chem. Pharm. Bull.* 33:1615-1619). Various enteric coating materials can be selected on the basis of testing to achieve an enteric-coated dosage form designed ab initio to have a preferable combination of dissolution time, coating thicknesses and diametral crushing strength. (Porter et al. (1970) *J. Pharm. Pharmacol.* 22:42p). It is contemplated that the enteric coating can be either food grade or pharmaceutical material which is generally used in the production of various drug or dietary supplements.

Depending on whether the synbiotic product is to be consumed by an adult human, child or animal (e.g., companion animal or livestock), it can be produced in various sizes and with various ingredients suitable for the intended recipient. For example, while a gel cap size of 0 or 1 may be suitable for humans, a gel cap size of 2, 3, 4, or 5 may be more suitable for a companion animal.

Further, because the probiotic and prebiotic components of the present invention are generally recognized as safe, they can be consumed one, two or three times daily or more.

The present invention also relates to a method for removing nitrogenous waste products from the blood of an individual with elevated levels of nitrogen-containing waste products. The method involves administering an effective amount of a synbiotic product of the present invention so that the levels of nitrogenous waste products in the blood are decreased or reduced, desirably to a normal range. For example, normal levels of creatinine in the blood are in the range of 0.6-1.2 mg/dL, whereas normal blood urea nitrogen (BUN) levels range from 7-18 mg/dL and normal uric acid levels in males and females is in the range of 2.1 to 8.5 mg/dL and 2.0 to 7.0 mg/dL, respectively. Further, a BUN/creatinine ratio of 5-35 is indicative of normal levels of nitrogenous waste products in the blood. As one of skill in the art can appreciate, means for determining the levels of nitrogenous wastes are well-known to the skilled laboratory clinician.

As synbiotic products of the present invention containing a *S. thermophilus* strain that secretes elevated levels of urease have been shown to reduce the levels of nitrogenous waste products in the blood of a stable model of chronic renal failure, these compositions are useful in the a method for treating or preventing renal failure. The method involves administering a synbiotic product of the present invention containing a *S. thermophilus* strain that secretes elevated levels of urease to a subject having or at risk of having renal failure. Subjects having or at risk of having renal failure include those with diabetic nephropathy, hypertensive nephrosclerosis, glomerulonephritis, interstitial nephritis, or polycystic kidney disease wherein nephron function is impaired thereby decreasing glomerular filtration rate. Desirably, an effective amount of a synbiotic product for treating renal failure is an amount sufficient to effect beneficial or desired results, including clinical results, and, as such, an effective amount of a synbiotic product is one which results in the alleviation or amelioration of one or more symptoms associated with renal failure (e.g., a build up of uremic solutes), diminishment of extent of disease, stabilized (i.e., not worsening) state of disease by supporting healthy bowel function, delay or slowing of disease progression, or amelioration or palliation of the disease state. Treatment can also mean prolonging survival as compared to expected survival if not receiving treatment. Typical signs or symptoms associated with renal failure It is further contemplated that compositions of the present invention containing microorganisms secreting elevated levels of urease may have further utility in the prevention or treatment of gout and kidney stones.

Example 1

Yogurt Food Product

A yogurt food product can be prepared from one gallon of commercially available whole, homogenized, pasteurized milk which is heated to boiling and quickly allowed to cool to approximately 45° C. To this is added approximately one ounce of yogurt starter culture containing lactic acid bacteria of the genus *Lactobacillus, Streptococcus, Bacillus* or *Bifidobacteria*. The mixture is mixed well and allowed to ferment at 37° C. for 10 to 12 hours. One or more prebiotics, whole fruit additives, flavoring, sweetening agents, binders, or other additives can be combined and added to the yogurt to obtain a product of desired consistency or to suit the palette of the prospective consumer. In one embodiment of the present invention, a food product comprises components to meet the special dietary needs of individuals with renal insufficiency.

Example 2

Health Bar

Health bars can be prepared by combining various excipients, such as binders, additives, flavorings, colorants and the like, along with the prebiotic (e.g., *Lactobacillus, Streptococcus, Bacillus* or *Bifidobacteria*) and probiotic components, and mixing to a plastic mass consistency. The mass is then either extruded or molded to form "candy bar" shapes that are then dried or allowed to solidify to form the final product.

Example 3

Medical Food

A medical food can be prepared by combining rolled oats, dehydrated apples, honey, inulin, carob flour, cinnamon, sugar, vanilla extract, and lyophilized cultures of *L. acidophilus* and or *L. fermentum*, a *Bifidobacteria*, and *Streptococcus thermophilus* ($10^8$-$10^{10}$ cfu each). These ingredients are mixed in appropriate proportions with a prebiotic and formed into a rectangular bar approximately 12.5 to 15 centimeters in length, 3 to 4 centimeters in width and 1 centimeter in height and placed into a sterile vacuum oven for 12 to 24 hours to obtain an edible food product of the desired consistency.

Example 4

Dietary Supplement

A dietary supplement of the present invention can be prepared by combining lactic acid bacteria such as *Lactobacillus* acidophilus (10 to 15%) and *Bifidobacteria longum* (10-15%), and a urease-secreting microorganism such as *Streptococcus thermophilus* (70-80%), aseptically freeze-drying the bacteria and combining the processed bulk bacteria (e.g., about 50% of the total synbiotic product weight) with the prebiotic component (e.g., 5-50% by weight of each of lactulose, psyllium husks, and BENEFIBER, wherein the final prebiotic component is about 45% of the total synbiotic product weight). Fillers such as magnesium stearate, talc and starch (e.g., about 5% of the total synbiotic product weight) are added to the prebiotic and probiotic components and enterically coated gel caps are produced according to the method of Kim et al ((1988) *J. Indust. Microbiol.* 3:253-257). Approximately 10 to 25 billion CFU of the freeze-dried microorganism is contained in each capsule (i.e., approximately 30 to 75 billion CFU microorganisms per gram) that is enterically coated with hydroxy-propylmethyl cellulose phthalate by spraying over a fluidized bed of capsules. The resulting dietary supplement has a low surface area, is relatively non-porous and can protect the contents therein from low pH as is found in the gastric environment for several hours, and will release the contents into the bowel wherein the pH is relatively neutral or slightly alkaline. Advantageously, approximately 90-95% of the microorganisms can survive to be released into the gastric environment.

Example 5

Pharmaceutical Product

A pharmaceutical product for persons suffering from renal insufficiency can be prepared by aseptically freeze-drying one or more probiotic microorganisms (e.g., a *Lactobacillus*, a *Bifidobacterium*, and a *Streptococcus*). The processed bulk microorganisms are then combined with the probiotic component and prepared as enterically coated capsules according to the method of Kim et al ((1988) supra) or tablets, powders, soft gels, gelcaps, or liquids according to standard methods. For example, the prebiotic and probiotic components in each capsule are enterically coated with hydroxy-propylmethyl cellulose phthalate by spraying over a fluidized bed of capsules. The resulting pharmaceutical product has a low surface area, is relatively non-porous and can protect the contents therein from low pH as is found in the gastric environment for several hours, and will release the contents into the bowel wherein the pH is relatively neutral or slightly alkaline.

Example 6

$5/6^{th}$ Nephrectomized Minipig Model of Chronic Uremia

The effects of a synbiotic composition of the present invention in the form of a gel cap product or formulation admixed with the pig chow were tested using an established model of chronic uremia (mild to moderate) in the Gottingen strain of miniature swine (Willis, et al. (1997) *J. Endourol.* 11(1):27-32). At sexual maturity (3 months of age) these pigs weigh 8-11 kg, and are about half the size of all other strains of minipigs. The pigs grow slowly and double their body weight in about 6 months.

In this uremic model, 5/6 of the renal mass is removed through bilateral flank incisions (McKenna, et al. (1992) *J. Urol.* 148(2 Pt 2):756-9). One kidney is entirely removed, and both poles of the contra lateral kidney are removed with the aid of electro-cautery (for scoring the renal capsule and about 2 mm of parenchyma), surgical staples, and Gel foam sutured over the exposed parenchyma of the remnant. The contra lateral kidney is removed during the same surgical procedure by gross dissection and ligation and section of the renal artery and vein and ureter. The pigs used in this analysis characteristically experienced a large, acute elevation of creatinine and Blood Urea Nitrogen (BUN) concentrations in plasma; followed by a decline over 1-2 weeks to values that stabilized well above baseline. These pigs maintained their appetite and stable uremia for 3-6 months, maintained or gained body weight, and behaved no differently than normal control pigs. Hematocrits declined slowly as the uremia progressed and hemoglobin concentrations also declined over time. After the surgery, the pigs were allowed to recover for 3-4 weeks prior to administering the synbiotic compositions.

Using this model, several different blinded synbiotic formulations in the form of gel caps or admixed with the pig chow were tested as gut-based therapy for uremia. Formulations administered with the pig chow did not demonstrate any significant differences either in BUN or creatinine values. However, $5/6^{th}$ nephrectomized mini pigs (n=6) given a formulation containing four microbial strains (*L. acidophilus, L. bulgaricus, B. longum* and *S. thermophilus;* $10 \times 10^9$ CFU/gel cap) exhibited continued body weight gains of approximately 31% and decreased BUN and creatinine levels of approximately 13% each. Similarly, two $5/6^{th}$ nephrectomized mini pigs given a formulation containing three microbial strains (*L. acidophilus, B. longum* and *S. thermophilus;* $10 \times 10^{10}$ CFU/gel cap) also showed a decrease in BUN (average 21%) and creatinine (average 29%) levels although the body weight of one mini pig increased (6%) and the other decreased (20%). Additional formulations were tested in the form of gel caps or admixed with food and in general the results indicated that oral treatment with a probiotic formulation effectively and significantly reduced plasma creatinine concentrations by 22.5±8.5% in a stable porcine model of chronic renal failure. Small sample size may have prevented detection of corresponding reductions in BUN and elevation of hematocrit.

Example 7

Animal Dosing of Synbiotic Gel Cap

Table 1 provides a suitable approximate dosage of a gel cap (e.g., as described in Example 4) for administration to an animal such as a companion animal.

TABLE 1

| Weight pounds (Kg) | Morning Dose | Evening Dose |
| --- | --- | --- |
| Less than 2.2 lbs (<1 Kg) | 1 | 0 |
| 2.2-4.4 lbs (1-2 Kg) | 1 | 1 |
| 4.4-8.8 lbs (2-4 Kg) | 2 | 1 |
| 8.8-17.6 lbs (4-8 Kg) | 2 | 1-2 |
| 17.6-35.2 lbs (8-16 Kg) | 2 | 2 |
| 35.2-70.4 lbs (16-32 Kg) | 2-3 | 2-3 |
| More than 70.4 lbs (>32 Kg) | 3 | 3 |

Example 8

Urease-Secreting Strains of Streptococcus thermophilus

This example discloses the isolation and selection of a high level urease-secreting strain of Streptococcus thermophilus. Three isolates of gram-positive, lactic acid-producing non-pathogenic cocci of Streptococcus thermophilus were isolated from various sources and designated KB4, KB19, and KB25. KB4 was isolated from a probiotic product, KB19 was isolated from a commercial yogurt product and KB25 from Dahi yogurt (from India).

Growth rates and urea hydrolysis of these bacteria in the intestinal pH range (pH 5.5, 6.3 and 7.5) were determined by transferring exponentially growing cultures of KB19, KB4 and KB25 into modified Artificial Intestinal Fluid M2 (AIF, US Pharmacopeia) supplemented with 100 mg/dL filter-sterilized urea, 100 µM $NiCl_2$, 10% MRS broth, dextrose to final concentration of 1%, and 0.3% yeast extract, wherein the initial cell density was $10^9$ cfu/mL. Pancreatin was omitted from the recipe to allow the evaluation of bacterial growth by direct OD600 nm measurement. Urea concentration in the supernatants (% of control) and growth (OD600 nm) were measured every 4 hours.

Concentration of urea in the supernatants of bacterial cultures was measured using the protocol and standards supplied with the Blood Urea Nitrogen Reagent Kit (535, Sigma, St. Louis, Mo.). Urea hydrolysis was monitored by comparing urea-nitrogen concentrations in bacterial supernatants to appropriate control medium incubated in the same conditions and expressed as percent of control. Four to nine independent experiments were conducted and Student t-test was used for statistical analysis.

Under similar assay conditions, exponentially growing cultures of KB19, KB4 and KB25 were inoculated into AIF M2, pH 6.3, supplemented with 100 mg/dL urea and with or without 100 µM $NiCl_2$ at initial cell density of $10^9$ cfu/mL to determine whether the growth and rates of urea hydrolysis by these strains was dependent on the additional Ni++. Urea concentration in the supernatants as a % of control and growth (OD600 nm) were measured every 4 hours. Four to nine independent experiments were conducted and Student t-test was used for statistical analysis.

Similarly, it was determined whether the growth and rate of urea hydrolysis of these strains was dependent on urea concentration. Under similar growth conditions exponentially growing cultures of KB19, KB4 and KB25 were inoculated into AIF M2, pH 6.3, supplemented with 100 µM NiCl2 and 100, 200, or 300 mg/dL urea. Urea concentration in the supernatants as a % of the control and growth (OD600 nm) were measured every 4 hours. Four to nine independent experiments were conducted and Student t-test was used for statistical analysis.

The survivability of these KB19, KB4 and KB25 was determined in artificial gastric juice in the presence and absence of urea and dextrose. The average loss in viable cell count after exposure to artificial gastric juice (logs cfu/mL) is shown in Table 2.

TABLE 2

| PH/Additive | KB19 | KB4 | KB25 |
|---|---|---|---|
| 1.4 | 7 | 7 | 7 |
| 2.0 | 7 | 7 | 7 |
| 2.5 | 3 | 4 | 4 |
| 2.5/Urea | 3 | 4 | 4 |
| 2.5/Dextrose | 3 | 3 | 3 |
| 2.5/Urea + Dextrose | 3 | 3 | 3 |
| 3.0 | 2 | 2 | 3 |
| 3.0/Urea | 2 | 3 | 3 |
| 3.0/Dextrose | 1 | 2 | 3 |
| 3.0/Urea + Dextrose | 1 | 2 | 2 |

Initial cell density was 107 cfu/mL. Urea and dextrose concentrations were 10 mg/mL and 1%, respectively.

Further it was determined whether the nutrient composition and availability had an affect on growth and urea hydrolysis by KB19, KB4, and KB25. Each strain was grown for 24 hours at 37° C. and pH 6.0 in the presence or absence of 100 mg/dL of urea and combinations of nitrogen and carbon sources. The results of this analysis are shown in FIG. 1.

Further analysis of S. thermophilus KB19 indicated that this strain could survive a 3 hour exposure to gastric juice, pH 3.0, followed by a 3 hour exposure to 0.3% oxgal, pH 6.0, with only 1 log loss in viability. Remaining viable cells were able to proliferate in AIF M2, pH 6.0, supplemented with 230 mg/dL urea and completely hydrolyzed the urea within less than 18 hours (n=4). All test solutions were supplemented with 230 mg/dL urea and 1% dextrose.

Collectively, these analyses indicated that all three strains studied proliferated in the fed state AIF medium in the pH range from 5.5 to 7.5, characteristic of colon environment; they could all use urea as a sole nitrogen source; and they each catabolized urea in the presence of other nitrogen sources. Urea hydrolysis was growth and pH dependent. Under the conditions tested, the rate of urea hydrolysis was strain-dependent in tests of pH stability: KB19=KB25>KB4; Ni requirement: KB25>KB19>KB4; urea hydrolysis for over 300 mg/dL: KB19=KB25>KB4; and specific nutrients: KB19>KB25>KB4. Further, there was strain-dependent results relating to survivability, wherein in tests of gastric juice stability: KB19>KB4>KB25; and bile stability: KB19>KB4>KB25.

In view of the desirable traits exhibited by S. thermophilus KB19 it was further determined, using a disc-diffusion test, that K19 was sensitive to Spectinomycin (100 µg), Kanamycin (30 µg), Chloramphenicol (30 µg), Spectinomycin (100 µg), Penicillin (10 IU), Carbenicillin (100 µg), Doxycycline (30 µg), and neomycin (30 µg).

To further enhance the levels of urease secreted by strain K19, this strain was trained on increasing levels of urea as described herein.

What is claimed is:

1. A composition comprising Lactobacillus acidophilus, Streptococcus thermophilus, Bifidobacterium longum, and psyllium husks, wherein said composition is enterically coated and the Streptococcus is selected for the ability to reduce urea concentrations from 300 mg/dL to 20 mg/dL within 24 hours at pH 6.3.

2. The composition of claim 1, wherein the bacteria comprise 20% to 70% of the total weight of the composition.

3. The composition of claim 1, wherein the psyllium husks comprise 20% to 70% of the total weight of the composition.

4. A method of removing nitrogenous waste products comprising administering an effective amount of a composition of claim 1.

5. A method of treating renal failure comprising administering an effective amount of a composition of claim 1.

* * * * *